(12) United States Patent
Kapadia

(10) Patent No.: US 10,213,584 B2
(45) Date of Patent: Feb. 26, 2019

(54) METHOD AND APPARATUS FOR GUIDING A CATHETER

(71) Applicant: THE CLEVELAND CLINIC FOUNDATION, Cleveland, OH (US)

(72) Inventor: Samir Kapadia, Chagrin Falls, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 336 days.

(21) Appl. No.: 14/783,158

(22) PCT Filed: Apr. 10, 2014

(86) PCT No.: PCT/US2014/033612
§ 371 (c)(1),
(2) Date: Oct. 8, 2015

(87) PCT Pub. No.: WO2014/169097
PCT Pub. Date: Oct. 16, 2014

(65) Prior Publication Data
US 2016/0058978 A1 Mar. 3, 2016

Related U.S. Application Data

(60) Provisional application No. 61/974,539, filed on Apr. 3, 2014, provisional application No. 61/810,500, filed on Apr. 10, 2013.

(51) Int. Cl.
*A61M 25/01* (2006.01)
*A61M 25/09* (2006.01)
(Continued)

(52) U.S. Cl.
CPC ...... *A61M 25/09041* (2013.01); *A61M 25/01* (2013.01); *A61M 25/09* (2013.01);
(Continued)

(58) Field of Classification Search
CPC . A61M 25/09041; A61M 25/01; A61M 25/09
See application file for complete search history.

(56) References Cited

U.S. PATENT DOCUMENTS 6,440,161 B1 8/2002 Madrid et al.
2009/0306757 A1* 12/2009 Meyer .............. A61M 25/0105
623/1.11
(Continued)

FOREIGN PATENT DOCUMENTS

GB 2432319 A 5/2007
WO 9960915 A2 12/1999
(Continued)

OTHER PUBLICATIONS

International Search Report and Written Opinion for PCT/US2014/033612, dated Jul. 10, 2014, pp. 1-16.

*Primary Examiner* — Nathan R Price
*Assistant Examiner* — Dung T Ulsh
(74) *Attorney, Agent, or Firm* — Tarolli, Sundheim, Covell & Tummino LLP

(57) ABSTRACT

An apparatus (100) for guiding a catheter within a patient's body, the apparatus comprising: a first wire (112) having longitudinally spaced distal and proximal first wire ends (114,116)) separated by a first wire body; a catheter (102) having longitudinally spaced distal and proximal catheter ends (130,132) separated by a catheter body having a catheter lumen (136) extending longitudinally therethrough between the distal and proximal catheter ends, the catheter having a catheter aperture (138) extending substantially laterally through the catheter body at a location proximally adjacent to the distal catheter end; a second wire (120) having longitudinally spaced distal and proximal second wire ends (122,124) separated by a second wire body.

5 Claims, 17 Drawing Sheets

(51) Int. Cl.
*A61M 25/10* (2013.01)
*A61M 25/00* (2006.01)

(52) U.S. Cl.
CPC ............... *A61M 2025/0063* (2013.01); *A61M 2025/018* (2013.01); *A61M 2025/0177* (2013.01); *A61M 2025/1045* (2013.01)

(56) References Cited

U.S. PATENT DOCUMENTS

2009/0312745 A1* 12/2009 Goldfarb ........... A61M 25/0041
                                                                  604/514
2016/0058978 A1*  3/2016 Kapadia ................ A61M 25/01
                                                                  604/510
2017/0135833 A1*  5/2017 Syed ........................ A61F 2/954

FOREIGN PATENT DOCUMENTS

| WO | 0103762 A1 | 1/2001 |
| WO | 0145785 A2 | 6/2001 |
| WO | 02072186 A2 | 9/2002 |
| WO | 2005112798 A2 | 12/2005 |
| WO | 2006043133 A2 | 4/2006 |
| WO | 2011109067 A1 | 9/2011 |
| WO | 20121004511 A1 | 9/2012 |

* cited by examiner

US 10,213,584 B2

METHOD AND APPARATUS FOR GUIDING A CATHETER

RELATED APPLICATION

This application claims priority from U.S. Provisional Application No. 61/810,500, filed 10 Apr. 2013, and from U.S. Provisional Application No. 61/974,539, filed 3 Apr. 2014, the subject matter of both of which is incorporated herein by reference in its entirety and is also provided in the Appendix, which forms an integral part of this disclosure.

TECHNICAL FIELD

This invention relates to apparatuses and methods for guiding and/or directing a catheter or other sheath having a lumen into a desired position within a patient's body.

BACKGROUND

Because of tortuous anatomy and, often, small work areas, it may be difficult for a surgeon to place a wire or catheter "around a corner" or otherwise provide a cross over feature which allows access to a body lumen other than the body lumen through which the wire, catheter, or other sheath having a lumen was inserted into the patient's body.

SUMMARY

In an embodiment, a method for guiding a catheter within a patient's body is described. A distal end of a first wire is inserted into a first body lumen. The distal end of the first wire is advanced through the first body lumen toward an intersection of the first body lumen with second and third body lumens. The distal end of the first wire is directed into the second body lumen. A distal end of the catheter is inserted into the first body lumen. The first wire is associated with the catheter. The distal end of the catheter, guided by the associated first wire, is advanced through the first body lumen toward an intersection of the first body lumen with second and third body lumens. A distal end of a second wire is inserted into a lumen of the catheter. The distal end of the second wire is advanced through the catheter toward the intersection of the first body lumen with the second and third body lumens. With the catheter, the distal end of the second wire is directed into the third body lumen.

In an embodiment, an apparatus for guiding a catheter within a patient's body is provided. A first wire has longitudinally spaced distal and proximal first wire ends separated by a first wire body. A catheter has longitudinally spaced distal and proximal catheter ends separated by a catheter body having a catheter lumen extending longitudinally therethrough between the distal and proximal catheter ends. The catheter has a catheter aperture extending substantially laterally through the catheter body at a location proximally adjacent to the distal catheter end. A second wire has longitudinally spaced distal and proximal second wire ends separated by a second wire body. The catheter lumen selectively accepts at least a portion of the first and second wires therethrough. The catheter aperture selectively accepts at least a portion of the first wire body therethrough to place the distal first wire end outside the catheter lumen concurrently with at least a portion of the second wire body extending from the distal catheter end to place the distal second wire end outside the catheter lumen.

BRIEF DESCRIPTION OF THE DRAWINGS

For a better understanding of the invention, reference may be made to the accompanying drawings, in which.

DESCRIPTION OF EMBODIMENTS

Figure 1:
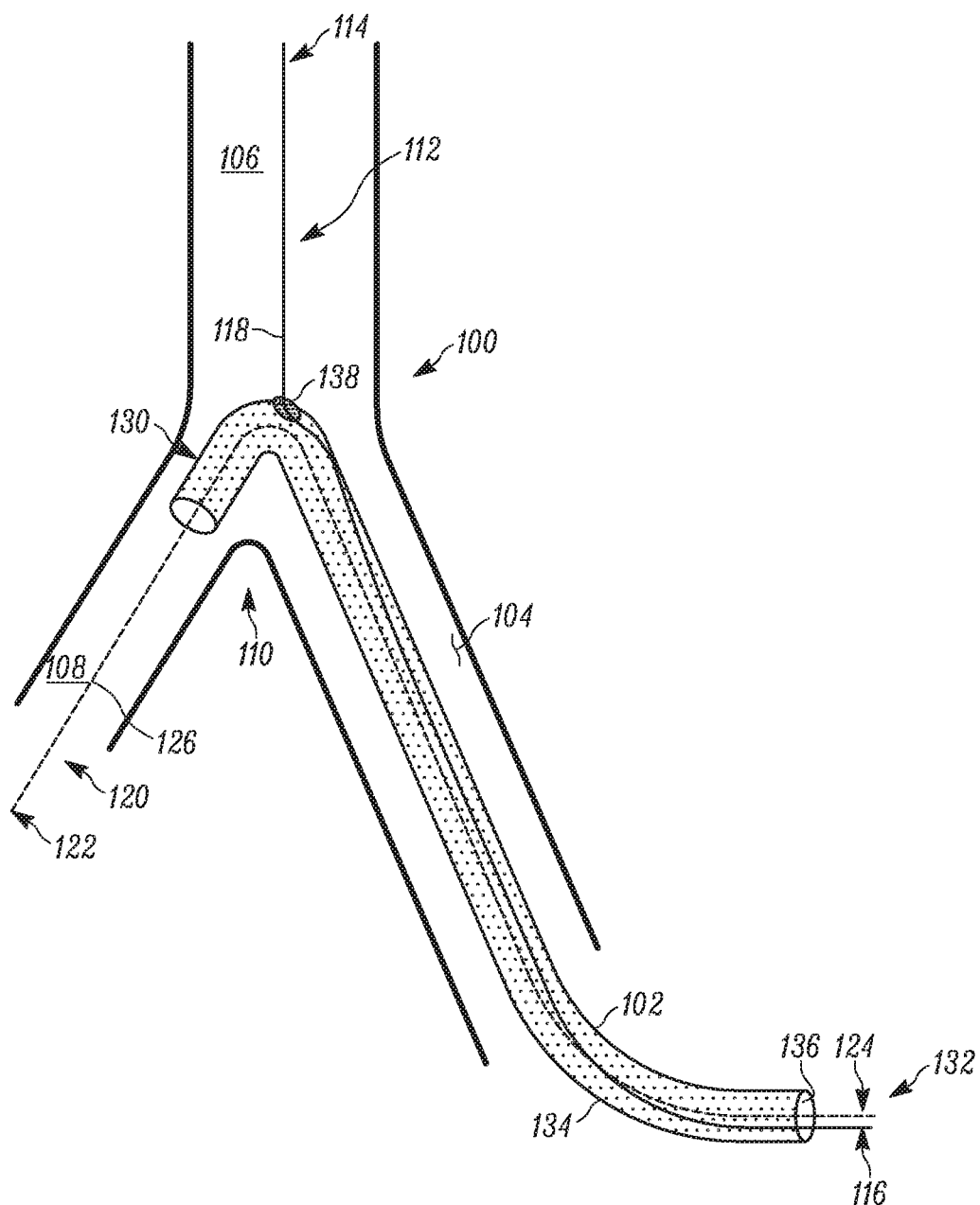
FIG. 1 is a schematic side view of one embodiment in an example use environment.

FIG. 1 depicts an apparatus 100 for guiding a cross over sheath, such as catheter 102, within a patient's body. The portion of the patient's body shown as an example use environment in FIG. 1 includes an left common iliac artery (first body lumen 104), an abdominal aorta (second body lumen 106), and a right common iliac artery (third body lumen 108). The first, second, and third body lumens 104, 106, 108 meet at a lumen intersection 110. The catheter 102 and other structures of the apparatus 100 can be guided or controlled for any desired reason, and into any desired placement, for a particular application of the present invention.

Figure 2:
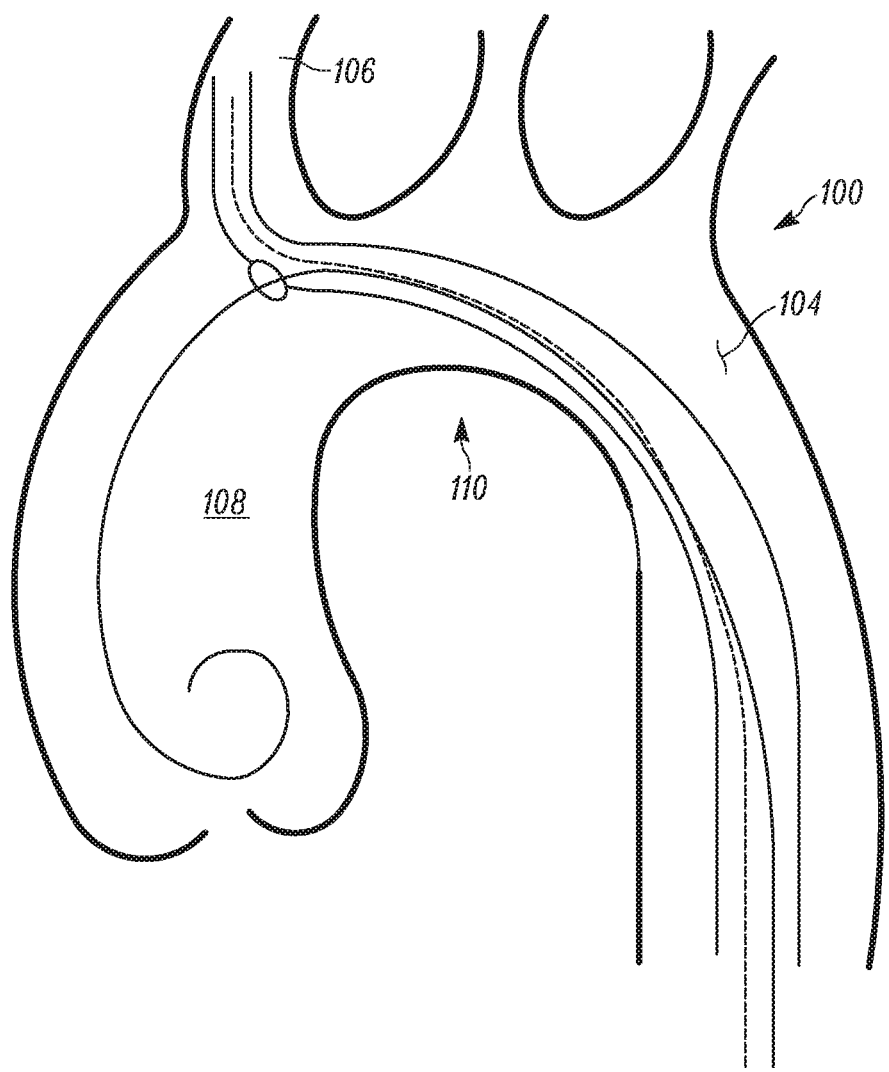
FIG. 2 is a schematic side view of the embodiment of FIG. 1 in another example use environment.
Figure 3:
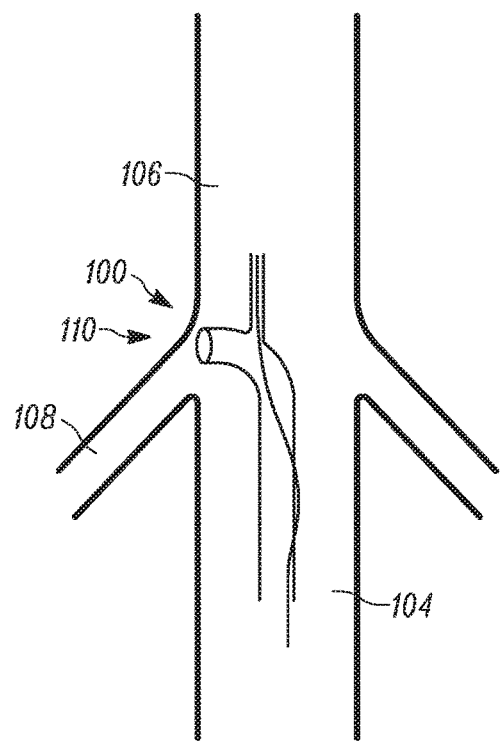
FIG. 3 is a schematic side view of the embodiment of FIG. 1 in another example use environment.
Figure 4:
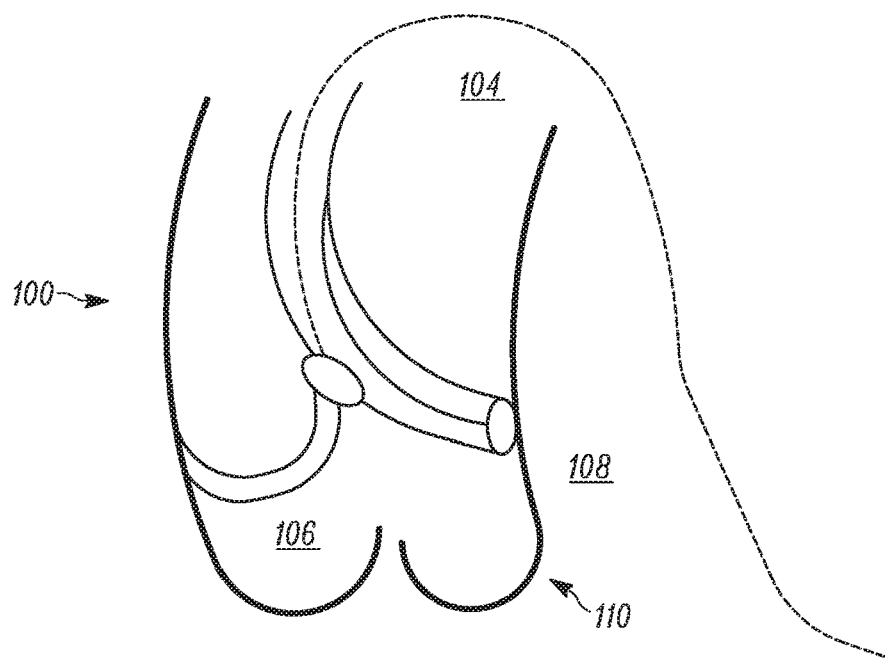
FIG. 4 is a schematic side view of the embodiment of FIG. 1 in another example use environment.

For example, FIG. 2 depicts an aortic arch use environment for the apparatus 100. As another example, FIG. 3 depicts a renal artery use environment for the apparatus 100 (shown in part in this Figure). As another example, FIG. 4 depicts a valvular use environment, wherein the third body lumen 108 is an ambient portion of the patient's body outside the first and second body lumens 104 and 106. Also shown in FIG. 4, one or both (here, the second body lumen 106) of the second and third body lumens 106 and 108 may be an extension of the first body lumen 104. In other words, there is not necessarily a anatomical separation between the first body lumen 104 and at least a chosen one of the second or third body lumens 106 or 108, but the second and/or third body lumens 106 and 108 may instead be defined/distinguished by one of ordinary skill in the art based upon the physical arrangement of the situation and the functions performed rather than by a strict structural separation.

The apparatus 100 may include a first wire 112 having longitudinally spaced distal and proximal first wire ends 114 and 116 separated by a first wire body 118. The apparatus 100 may also include a second wire 120 having longitudinally spaced distal and proximal second wire ends 122 and 124 separated by a second wire body 126.

The apparatus 100 may also include a catheter 102 having longitudinally spaced distal and proximal catheter ends 130 and 132 separated by a catheter body 134. The catheter body 134 has a catheter lumen 136 extending longitudinally therethrough between the distal and proximal catheter ends 130 and 132. The catheter 102 may have a catheter aperture 138 extending substantially laterally through the catheter body 134 at a location proximally adjacent to the distal catheter end 130. The phrase "proximally adjacent to" is used herein to indicate that the catheter aperture 138 does not intersect the distal catheter end 130 but is longitudinally spaced slightly proximally from the distal catheter end 130. "Proximally adjacent to" encompasses a spacing that is significantly closer to (e.g., a supermajority of the way to) the distal catheter end 130 than to the proximal catheter end 132. For certain example use environments discussed herein, at least a portion of the catheter aperture 138 may be located, for example, within two inches or less from the distal catheter end 130 of a catheter that is significantly longer than four inches total.

As shown in FIG. 1, the catheter lumen 136 may selectively accept at least a portion of the first and second wires 112 and 120 therethrough. For example, the catheter aperture 138 may selectively accept at least a portion of the first wire body 118 therethrough to place the distal first wire end 114 outside the catheter lumen 136, as shown, concurrently with at least a portion of the second wire body 126 extending from the distal catheter end 130 to place the distal second wire end 122 outside the catheter lumen 136. Optionally, the majority of the catheter body 134 may be located in the first body lumen 104 at the same time as the distal first and second wire ends 114 and 122 are placed as shown in FIG. 1.

Placement of the apparatus 100 into the abdominal aortic position shown in FIG. 1 will now be described with reference to FIGS. 5-14 and the flowchart of FIG. 15. In the below description, the first body lumen 104 is described as being a left common iliac artery 104, the second body lumen 106 is described as being an abdominal aorta 106, and the third body lumen 108 is described as being a right common iliac artery 108. However, one of ordinary skill in the art could provide a method and apparatus 100 suited for any other desired use environment, within a patient's body or in any other field of endeavour.

Figure 5:
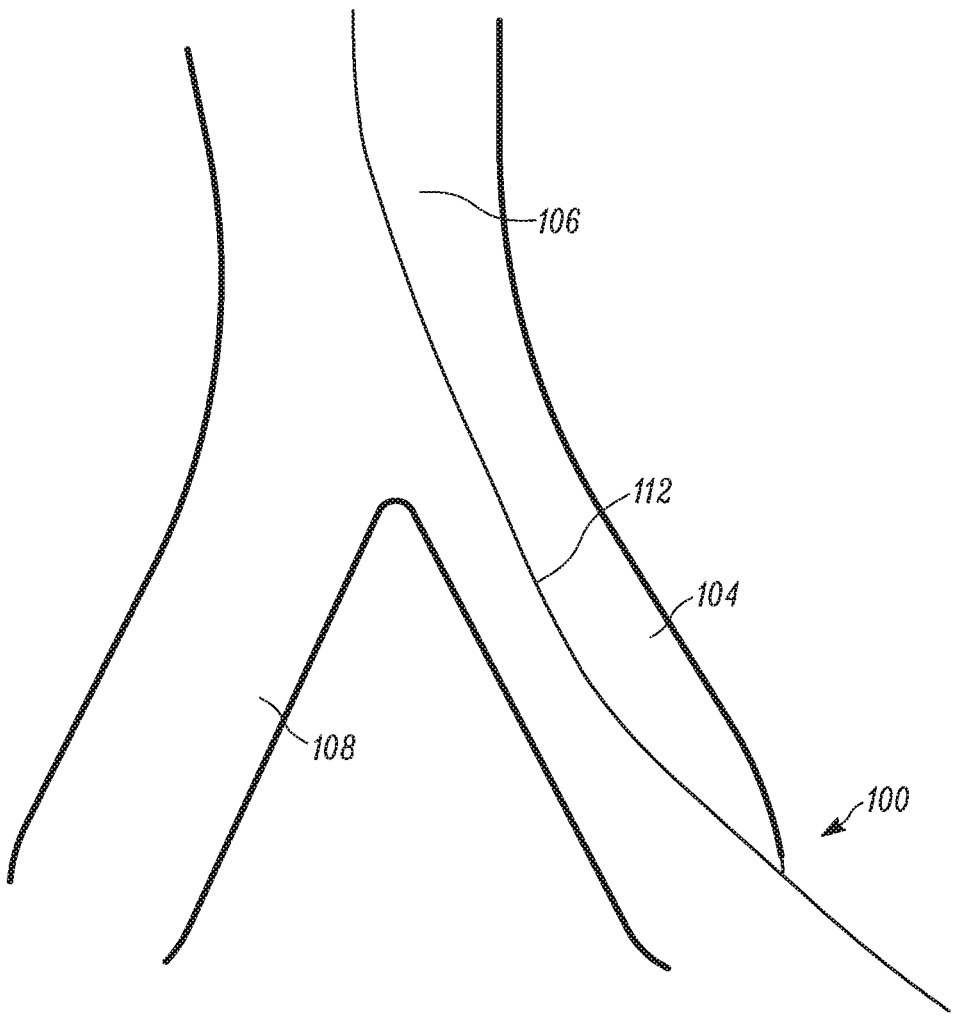
FIGS. 5-14 schematically illustrate an example sequence of use of the embodiment of FIG. 1.
Figure 15:
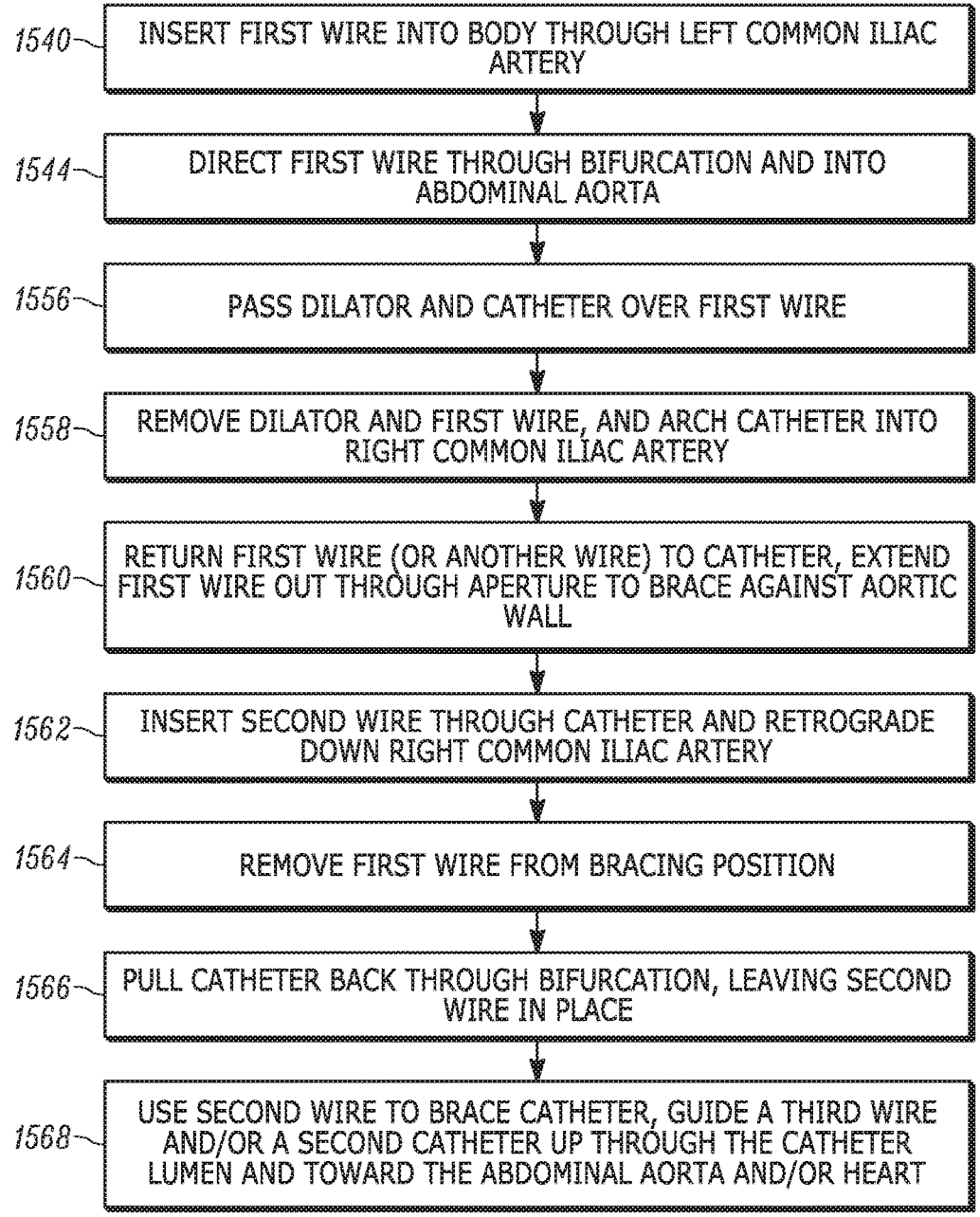
FIG. 15 is a flowchart of an example sequence of use of the embodiment of FIG. 1.

In first action block 1540 of FIG. 15, and as shown in FIG. 5, a first wire 112 is placed in the body through the left common iliac artery 104 and up into the abdominal aorta 106. For example, placing the apparatus 100 into the position shown in FIG. 5 could include inserting the distal first wire end 114 into the first body lumen 104, advancing the distal first wire end 114 through the first body lumen 104 toward a lumen intersection 110 (e.g., bifurcation) of the first body lumen 104 with the second and third body lumens 106 and 108, and directing the distal first wire end 112 into the second body lumen 106, as in second action block 1544 of FIG. 15.

Figure 6:
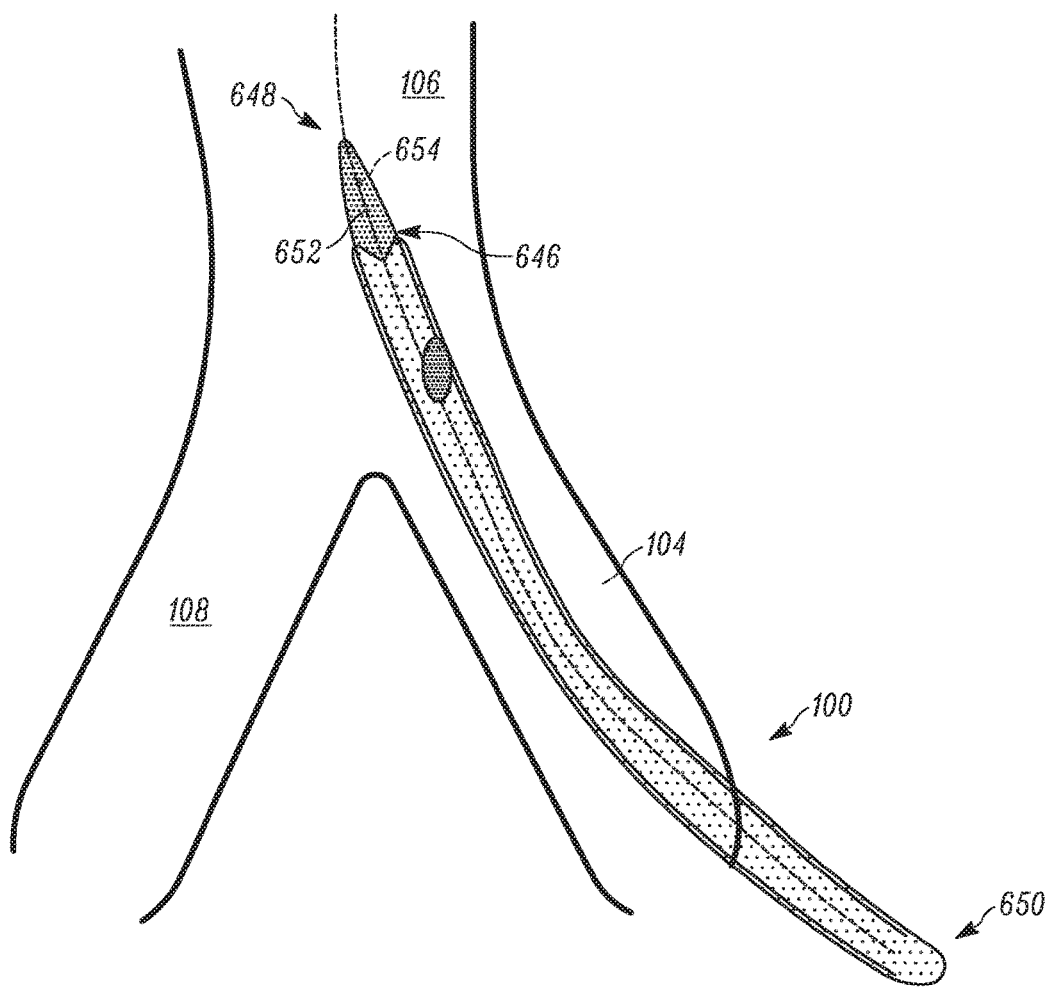

FIG. 6 shows the first wire 112 placed as in FIG. 5. The apparatus 100 shown in FIG. 6 includes a dilator 646 having longitudinally spaced distal and proximal dilator ends 648 and 650 separated by a dilator body 652 having a dilator lumen 654 extending longitudinally therethrough between the distal and proximal dilator ends 648 and 650. The dilator lumen 654 may selectively accept at least a portion of the first wire body 118 therethrough, as shown in FIG. 6. The catheter lumen 136, in turn, may selectively accept at least a portion of the dilator 646 therethrough. The optional dilator 646, when present, may be stiffer than the catheter 102 to assist with directing the catheter 102 through the patient's tortuous vasculature or other body lumen structure(s).

The dilator 646 and catheter 102 are passed over first wire 112 and into the position shown in FIG. 6, with the first wire 112 protruding from the distal catheter end 130 and the distal dilator end 648. This is described in third action block 1556 of FIG. 15. For example, a distal catheter end 130 could be inserted into the first body lumen 104 before, during, and/or after association of the first wire 112 with the catheter 102. The distal catheter end 130, guided by the associated first wire 112 and/or dilator 646, can then be advanced through the first body lumen 104 toward the lumen intersection 110 of the first body lumen 104 with the second and third body lumens 106 and 108. The catheter 102 can be, for example, a braided sheath catheter having an outer diameter of about 6 French and an inner diameter of about 4 French.

Figure 7:
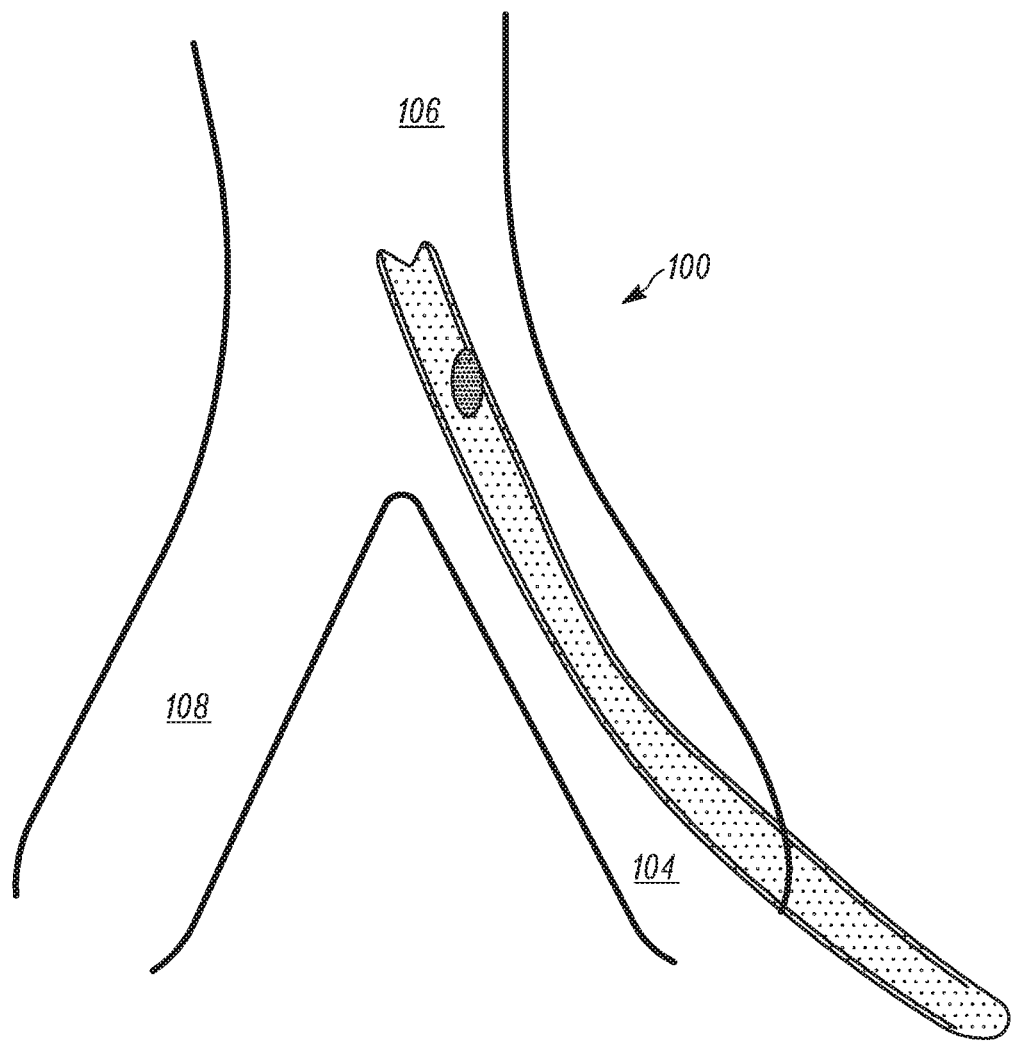

As shown in FIG. 7, the first wire 112 and/or the dilator 646 may be at least partially removed once the catheter 112 is in place in the first and second body lumens 104 and 106 as desired. Stated otherwise, the first wire 112 and/or the dilator 646 may be at least partially retracted from the patient's body while the catheter 102 is maintained in the patient's body.

Figure 8:
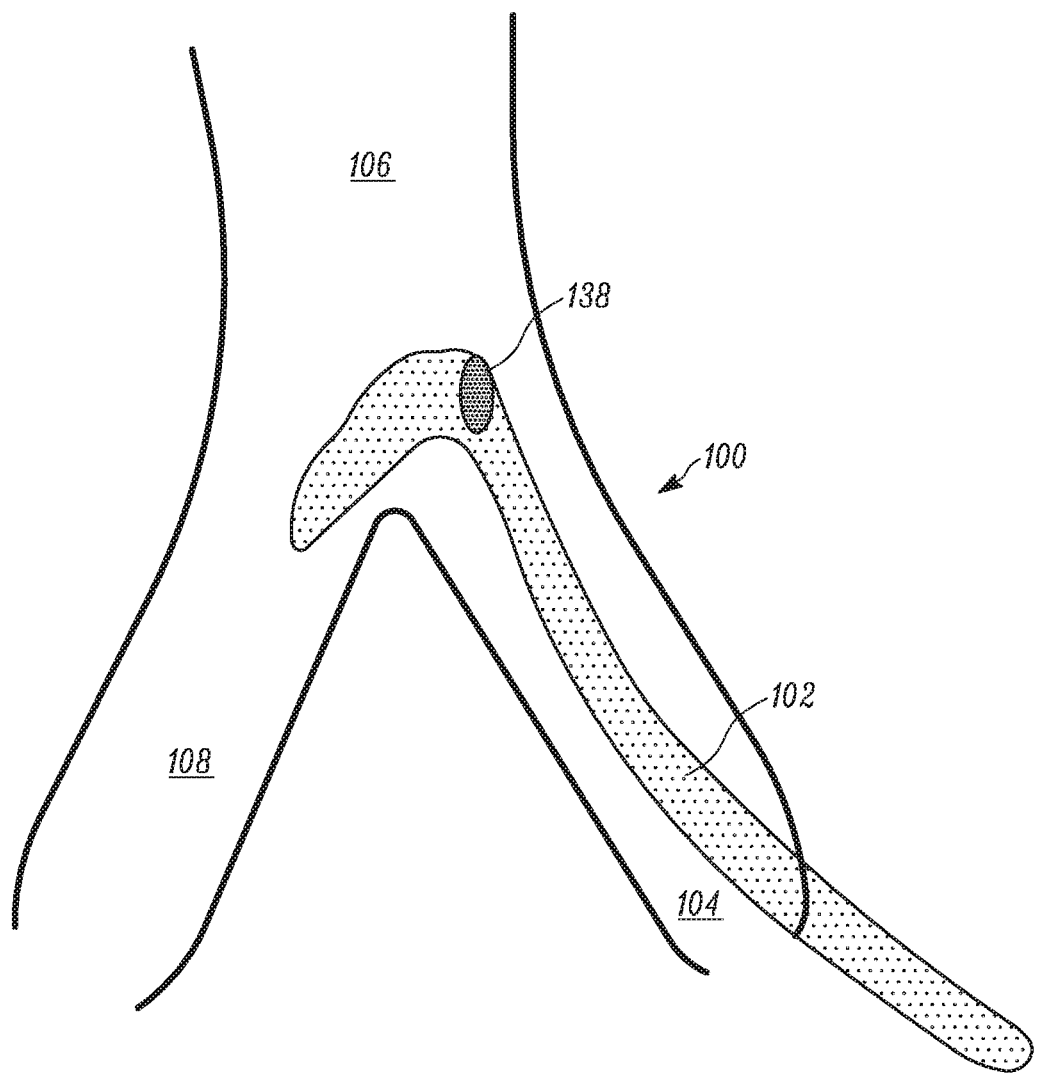

FIG. 8 depicts the catheter 102 having been steered into a bent or angled configuration pointing toward the right common iliac artery 108. The actions shown in FIGS. 7-8 are described in fourth action block 1558 of the FIG. 15 flowchart. For example, and as shown here, the distal catheter end 130 can be directed into the second body lumen 106, and then the distal catheter end 130 can be redirected from the second body lumen 106 to the third body lumen 108 with the catheter aperture 138, when present, opening on a side of the catheter body 134 which faces toward the second body lumen 106. The catheter 102 may be steerable, may be manipulated through the use of the first wire 112 and/or dilator 646, or may otherwise be placed into the position shown in FIG. 8 as desired.

Figure 9:
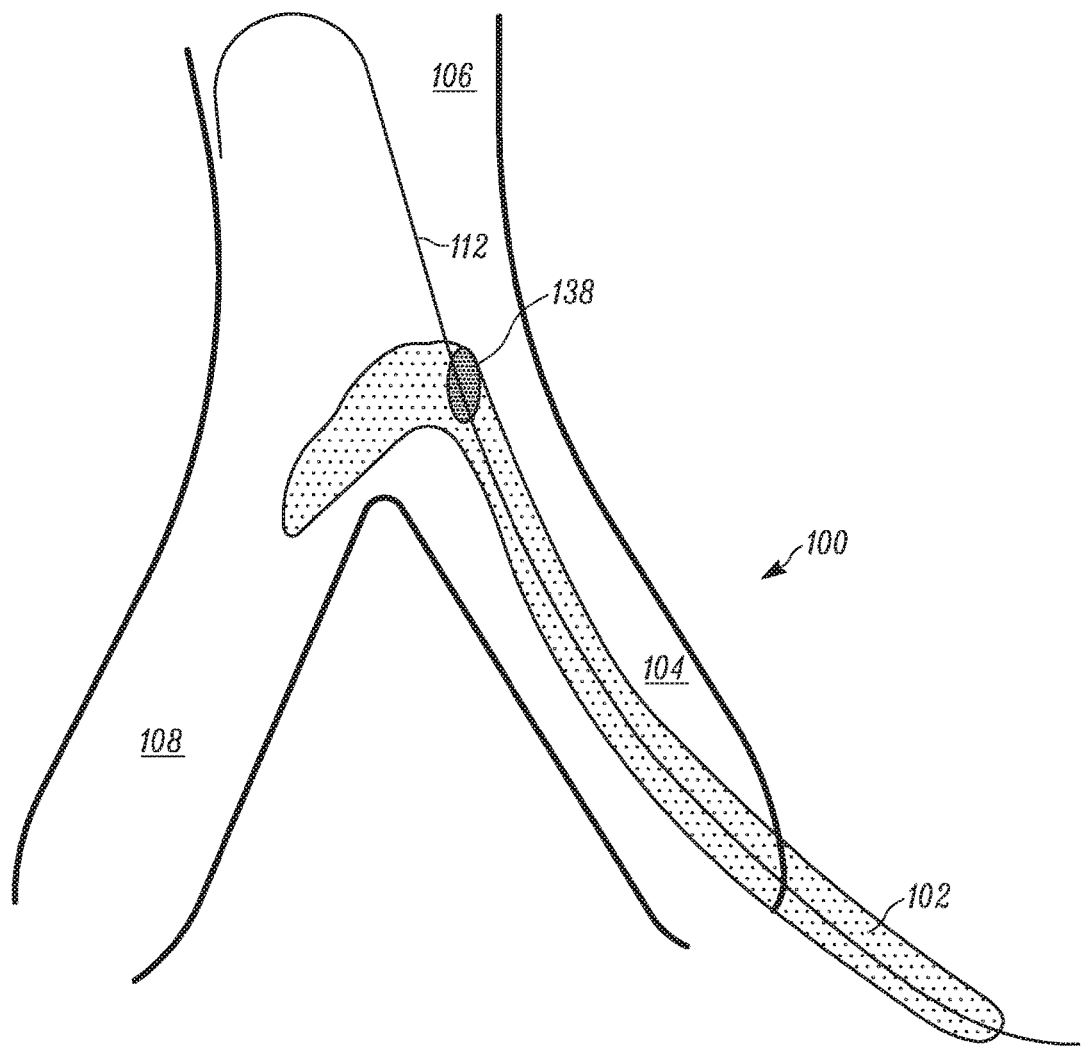

Once the catheter 112 is in the position of FIG. 8, the first wire 112, or another (separately provided) wire (not shown), can be passed back into the catheter 102 and out from the catheter aperture 138 to brace or stabilize the catheter against the aortic wall, as shown in FIG. 9 and described in fifth action block 1560 of the FIG. 15 flowchart. This "bracing" wire will described as first wire 112 hereafter, for clarity. The term "bracing" is used herein, for example, to indicate that a wall of the second body lumen 106 is contacted, and usually will be pushed against, with the distal first wire end 114 to at least partially control a position of the catheter 102 within the patient's body.

Figure 10:
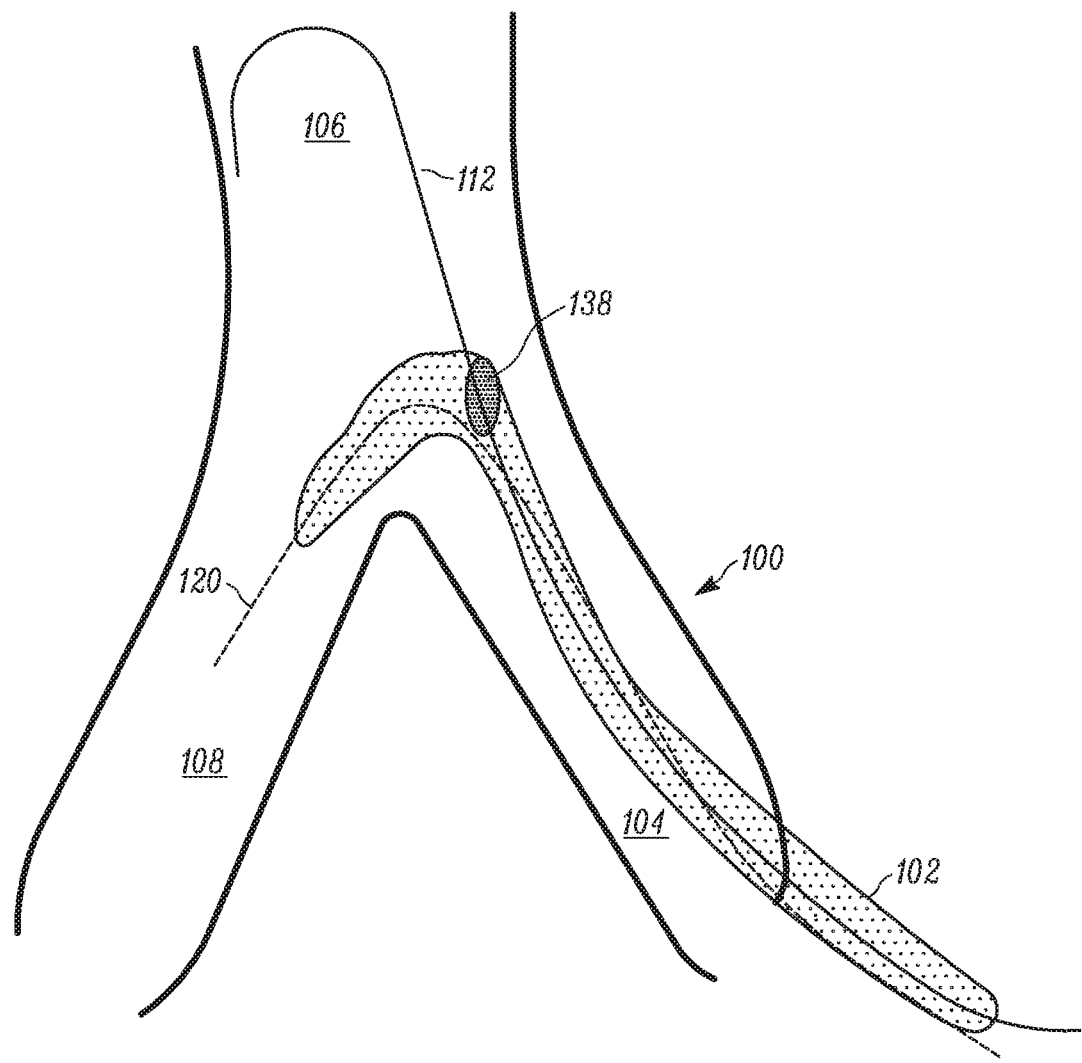
Figure 11:
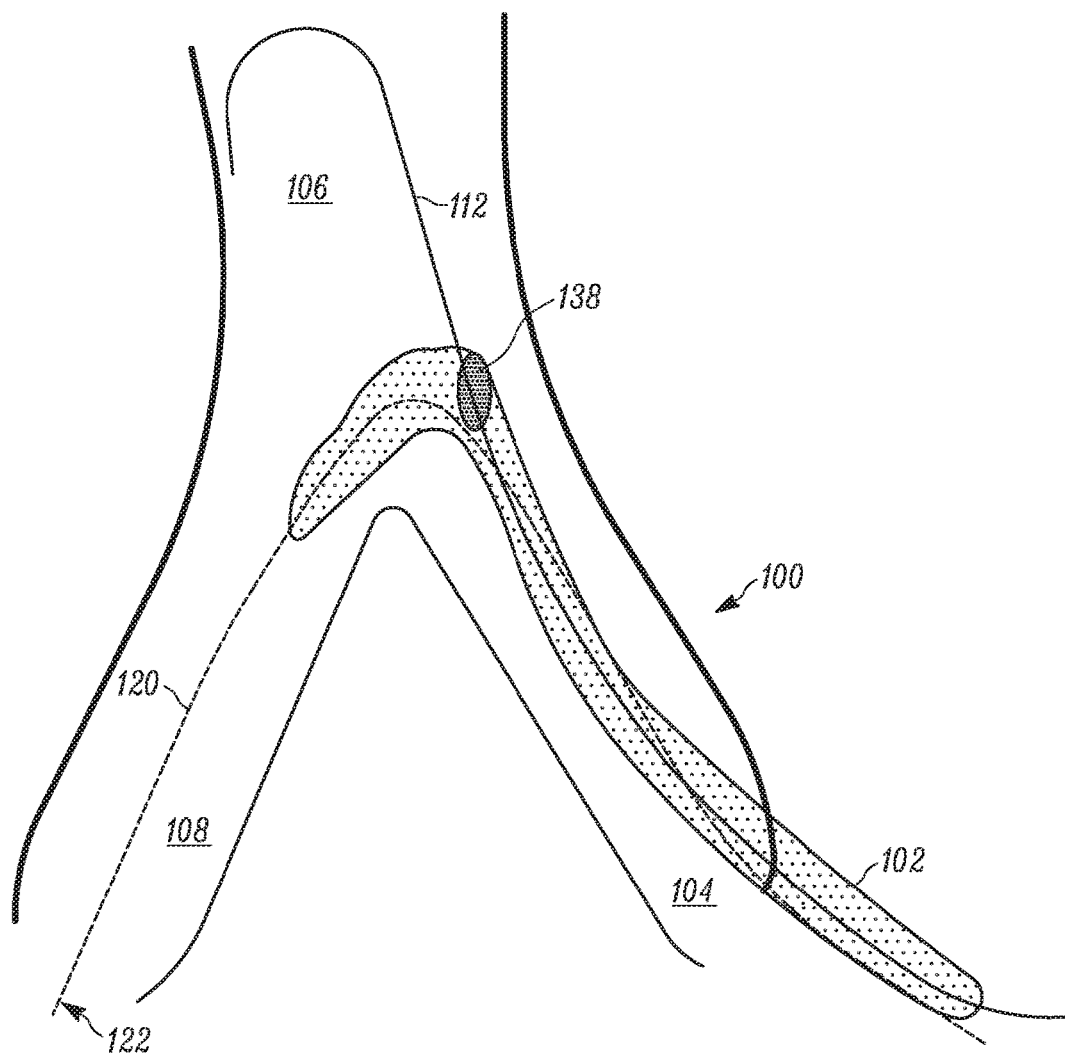

A second wire 120 (a.k.a., a cross over wire) is then passed through the first-wire-stabilized catheter 120 and inserted retrograde into the (contralateral) right common iliac artery 108, as shown in FIG. 10 and described in sixth action block 1562 of the FIG. 15 flowchart. In other words, a distal second wire end 122 can be inserted into the catheter lumen 136, the distal second wire end 122 is advanced through the catheter 102 toward the lumen intersection 110 of the first body lumen 104 with the second and third body lumens 106 and 108, and then the distal second wire end 122 is directed, with the catheter 102, into the third body lumen 108. FIG. 11 shows the second wire 120 more fully inserted retrograde into the third body lumen 108 than was depicted in FIG. 10.

Figure 10A:
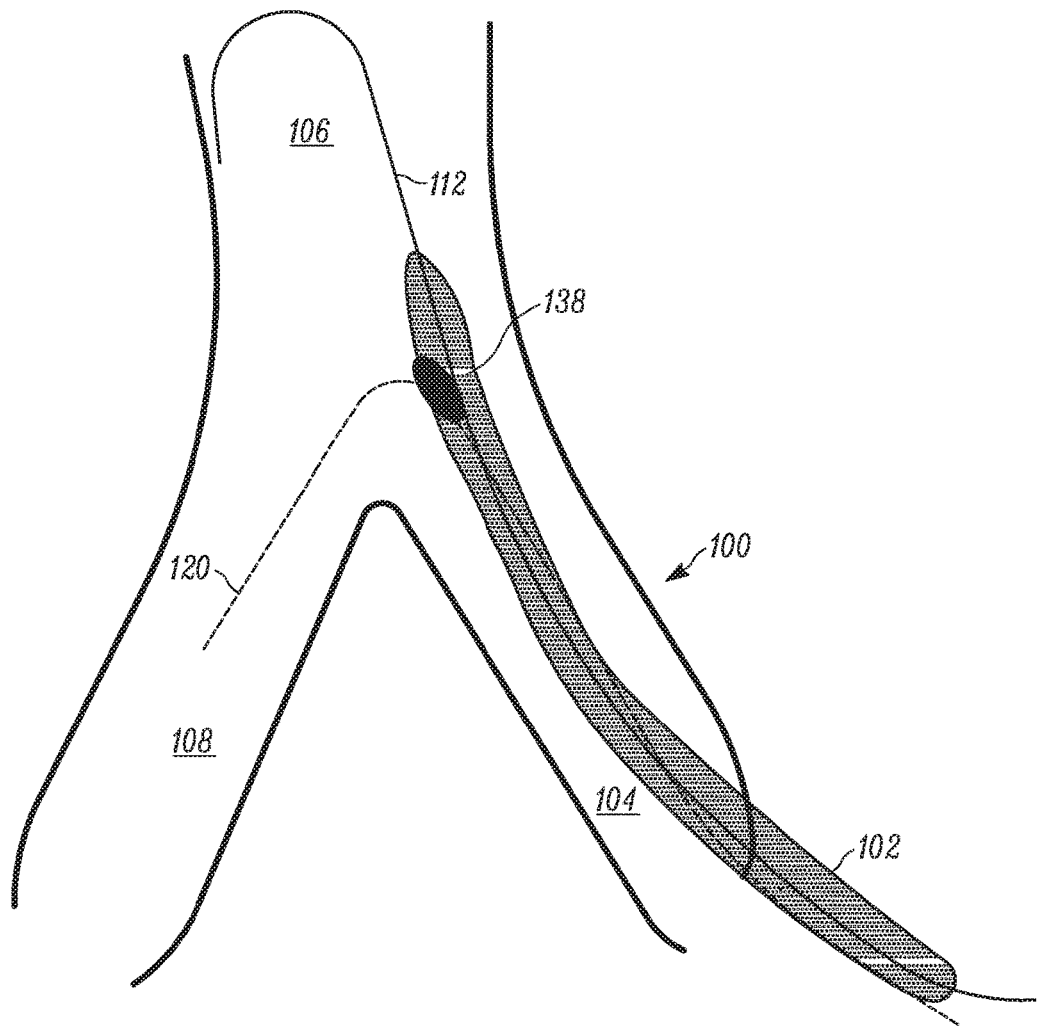

Optionally, the distal second wire end 122 exits the catheter 102 through the distal catheter end 130 as shown in the Figures. Alternatively, however, the catheter 102 and first wire 112 can be manipulated otherwise (as shown in FIG. 10A) so that the catheter aperture 138 "points" or opens toward the third body lumen 108. In such case, the distal catheter end 130 can be directed into the second body lumen 106, and the distal second wire end 122 can be directed out of the catheter lumen 136 through the catheter aperture 138 into the third body lumen 108. In such alternative circumstances, the first wire 112 may optionally be extended from the distal catheter end 130 into the second body lumen 106 to brace and help stabilize the catheter 102.

Figure 12:
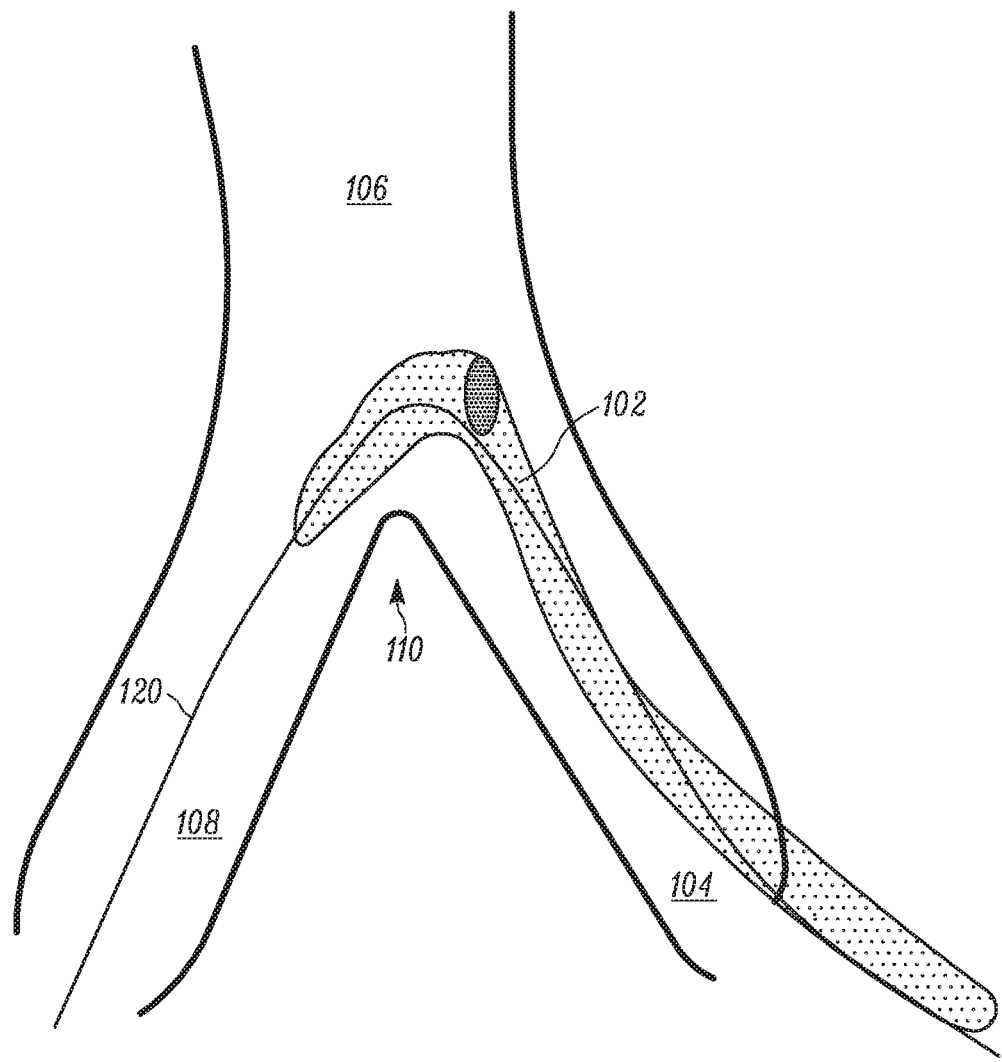
Figure 13:
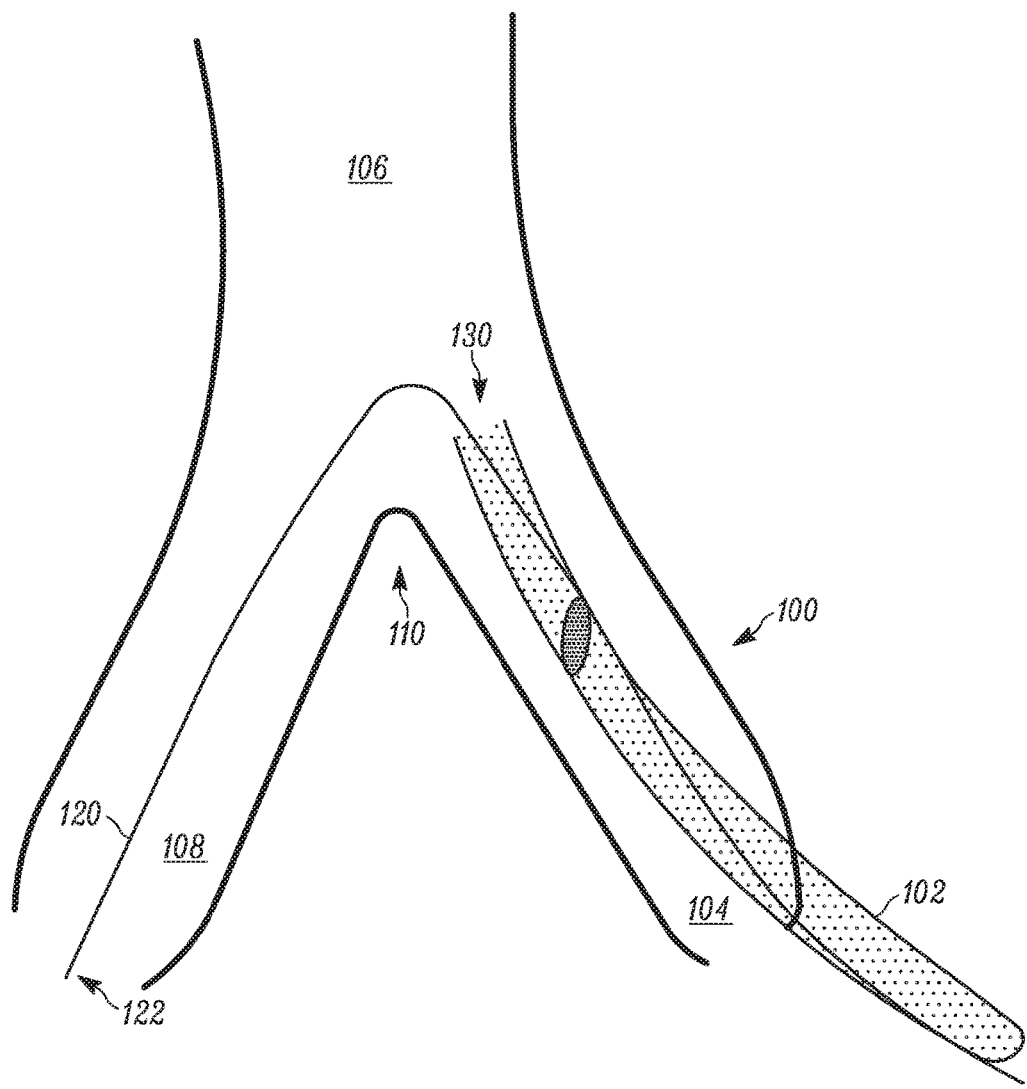

Once the second wire 120 is in place as shown in FIG. 11 (however such is achieved), the first wire 112 can be removed from the catheter 102, as described in seventh action block 1562 of the FIG. 15 flowchart, leaving the arrangement shown in FIG. 12. Optionally, the catheter 102 can also be at least partially retraced from the first body lumen 104. The second wire 120 can then be used directly to guide any desired structure, feature, or function through the lumen intersection 110 and into the third body lumen 108.

However, if desired, the second wire 120 can also or instead be used to assist with stabilizing the catheter 102 for placement of a wire or other structure through the catheter and up from the lumen intersection 110 into the second body lumen 106. For example, and as discussed in eighth action block 1566 of the FIG. 15 flowchart, the catheter 102 can be retracted through the lumen intersection 110 into the position shown in FIG. 13. That is, the distal catheter end 130 can be retracted into the first body lumen 104 with the distal second wire end 122 maintained in the third body lumen 106.

Figure 14:
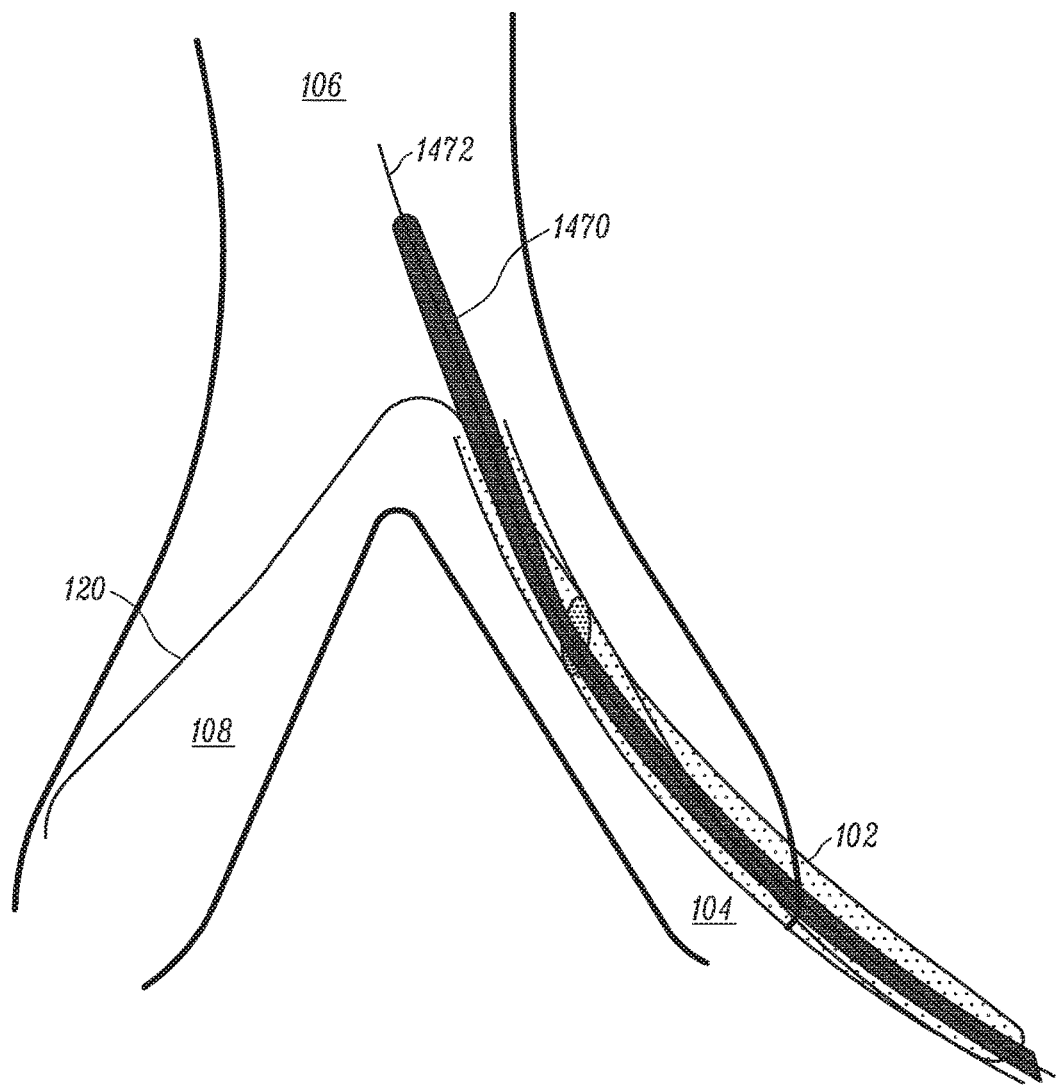

The second wire 120 can then be used, merely by its passive presence in the third body lumen 106 or by actively bracing against a wall of the third body lumen 106, as shown in FIG. 14 and described in ninth action block 1568 of the FIG. 15 flowchart, to help control a position of the catheter 102 in the first body lumen 104. For example, and as shown in FIG. 14, a second catheter 1470 and/or third wire 1472 (which may be the same wire previously referenced as the first wire 112) may be passed up through the catheter lumen 136 and toward the abdominal aorta 106 and/or, eventually, the heart—in such case, the second wire 120 can assist with appropriate positioning of the catheter 102 for passage of the second catheter 1470 and/or third wire 1472 therethrough. Stated differently, the second wire 120 can be used to help stabilize the sheath/catheter 102 to aid in the insertion of a working catheter 1470 and/or wire 1472 through the catheter 102 and toward the abdominal aorta 106 and portions of the cardiovascular system beyond.

Optionally, the second wire 120 can be used within the right common iliac artery 108 and femoral artery (not shown) to guide a wire (not shown) and/or a catheter (not shown) from a femoral cut-down up toward the abdominal aorta 106. The femorally-inserted wire and/or catheter can be used to help guide and deliver a stent, valve, graft, and/or any other desired surgical tool/prosthesis to the abdominal aorta 106, the heart, or any point of the cardiovascular system therebetween.

In an effort to keep the catheter lumen 136 clear, the first wire 112 could include a thicker distal portion (of any desired size such as, but not limited to, 0.035"—shown extending out of the catheter aperture 138) which helps with placement/guiding of the catheter 102 and a thinner, optionally stiffer proximal portion (of any desired size such as, but not limited to, 0.014"—shown located in the catheter lumen 136) to support the catheter 102 and provide an elongate "guidewire" type function while avoiding obstruction of the catheter lumen 136. This arrangement is shown in FIG. 16.

Figure 16:
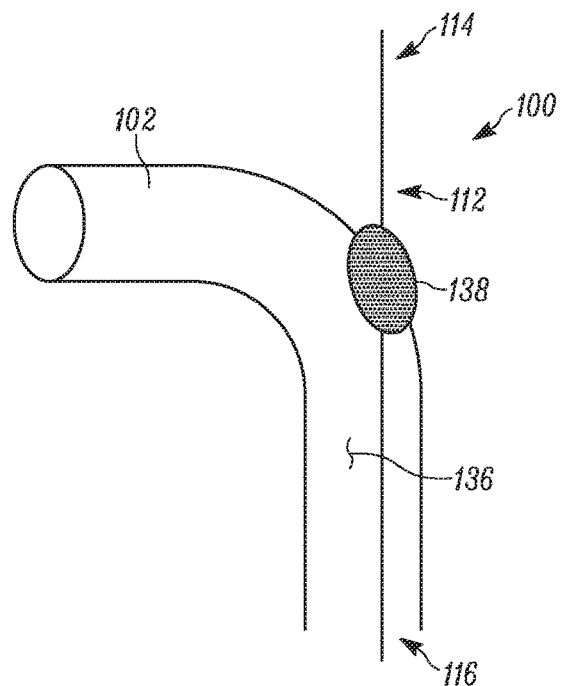
FIG. 16 is a schematic side view of the embodiment of FIG. 1 including an alternative configuration of a component.

In the apparatus 100 shown in FIG. 16, the "transition" between the thicker and thinner portions of the first wire 112 can occur at any desired point along that wire. The transition can be gradual (tapered) or abrupt (stepwise). The transition could be connected to the catheter 102 at/near the catheter aperture 138 in any desired manner, or may be "free-floating" and permitted to move longitudinally with respect to the catheter 102.

Figure 17:
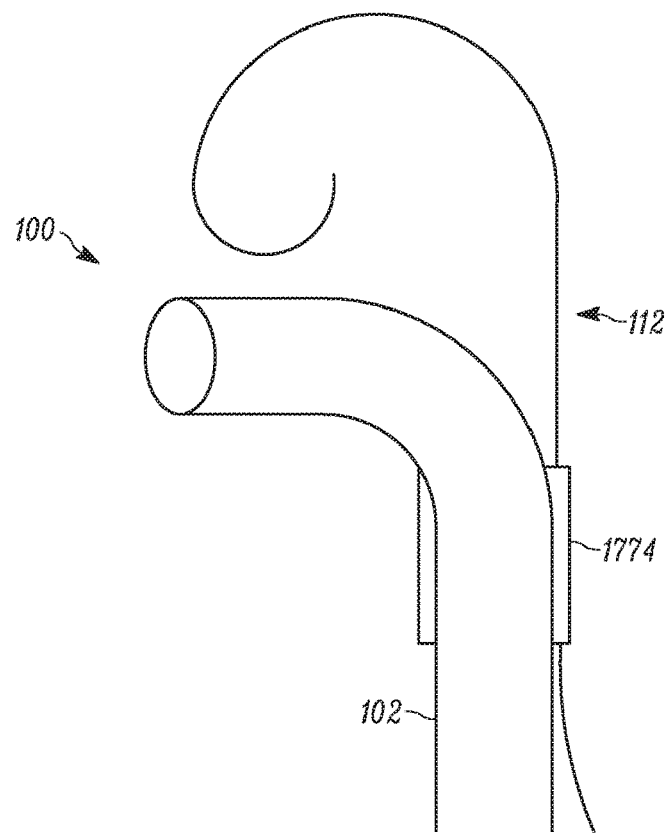
FIG. 17 is a schematic side view of the embodiment of FIG. 1 including an alternative configuration of a component.

In another embodiment of the present invention, shown in FIG. 17, the apparatus 100 could include an outer sleeve/cuff/collar 1174 (which could encircle part or all of the outer circumference of the catheter 102). This cuff 1774 could be used to attach first wire 112 to an outside of the catheter 102, again with the result of keeping the catheter lumen 136 open for use with second wire 120 (omitted from FIG. 17) or for any other reason.

For medical/anatomical reasons, the embodiment shown in FIG. 17 may be particularly useful in coronary use environments. The cuff 1774 could be placed into the depicted position of FIG. 17 before, during, and/or after insertion of the catheter 102 into the patient's body. Optionally, the cuff 1774 may slide with relation to the outer catheter surface in a "monorail" type manner. The cuff 1774 is shown as having a longitudinal extent ("cuff length") greater than its diameter, but the cuff 1774 length and diameter could have any desired relative dimensions, including a cuff length much smaller than the diameter to provide a "ring" type structure (very short cuff length) to the cuff 1774.

Figure 18:
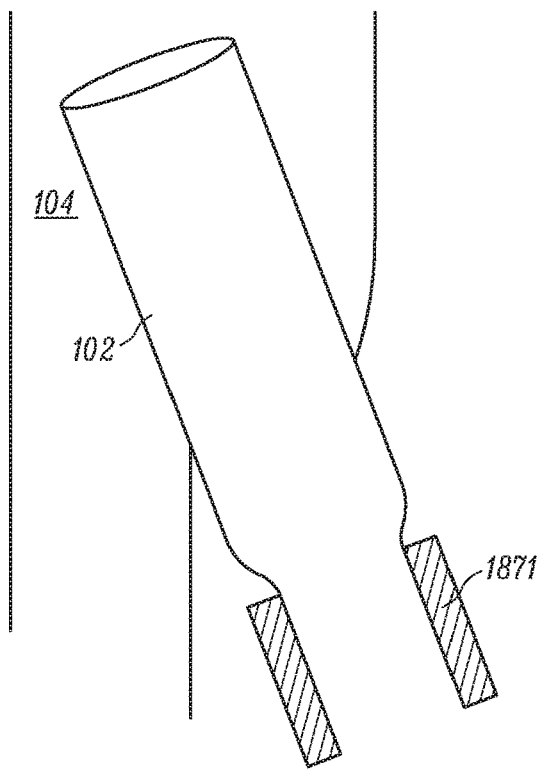
FIG. 18 is a schematic side view of the embodiment of FIG. 1 including an alternative configuration of a component.
Figure 19:
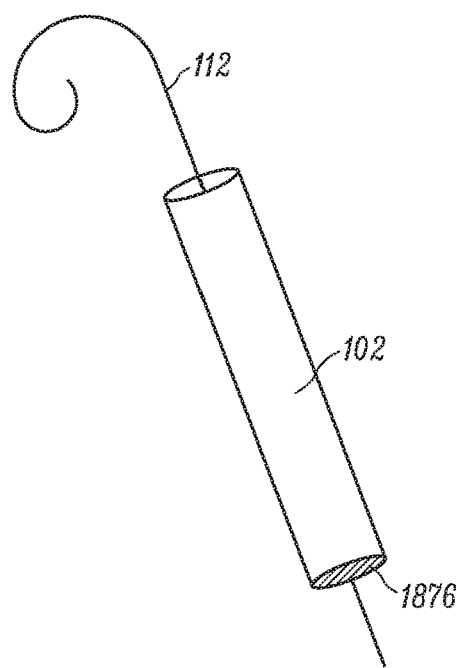
FIG. 19 is a schematic side view of the embodiment of FIG. 1 including the alternative configuration of FIG. 18.

Another aspect of the present invention is shown in FIGS. 18-19 and relates to the use of a stabilizer piece 1876 that is attached to the catheter 102 and is selectively slidable along the first wire 112. This stabilizer piece 1876 can be used, if needed, in a "monorail"-type manner to couple a first wire 112, placed alongside the catheter 102, to the catheter 102 itself. The combined apparatus 100 of the stabilizer piece 1876, catheter 102, and first wire 112 can be used similarly to the apparatus(es) 100 shown and described above.

While aspects of this disclosure have been particularly shown and described with reference to the example embodiments above, it will be understood by those of ordinary skill in the art that various additional embodiments may be contemplated. For example, the specific methods described above for using the apparatus 100 are merely illustrative; one of ordinary skill in the art could readily determine any number of tools, sequences of steps, or other means/options for placing the above-described apparatus, or components thereof, into positions substantively similar to those shown and described herein. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any component of the invention could be provided with a user-perceptible marking to indicate a material, configuration, at least one dimension, or the like pertaining to that component, the user-perceptible marking aiding a user in selecting one component from an array of similar components for a particular use environment. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one embodiment or configuration of the invention could be provided, singly or in combination with other structures or features, to any other embodiment or configuration, as it would be impractical to describe each of the embodiments and configurations discussed herein as having all of the options discussed with respect to all of the other embodiments and configurations. A device or method incorporating any of these features should be understood to fall under the scope of this disclosure as determined based upon the claims below and any equivalents thereof.

Other aspects, objects, and advantages of the invention can be obtained from a study of the drawings, the disclosure, and the appended claims.

Having described the invention, I claim:

1. A method for guiding a catheter within a patient's body, the method comprising:
    inserting a distal end of a first wire into a first body lumen;
    advancing the distal end of the first wire through the first body lumen toward an intersection of the first body lumen with second and third body lumens;
    directing the distal end of the first wire into the second body lumen;
    inserting a distal end of the catheter into the first body lumen;
    associating the first wire with the catheter to create an associated first wire;
    advancing the distal end of the catheter, guided by the associated first wire, through the first body lumen toward the intersection of the first body lumen with the second and third body lumens;
    inserting a distal end of a second wire into a lumen of the catheter;
    advancing the distal end of the second wire through the catheter toward the intersection of the first body lumen with the second and third body lumens;
    directing the distal end of the catheter into the third body lumen, including
        directing the distal end of the catheter into the second body lumen by advancing the distal end of the catheter, guided by the associated first wire, into the second body lumen,
        providing an aperture substantially laterally through a sidewall of the catheter proximally adjacent to the distal end of the catheter,
        at least partially withdrawing the first wire from the catheter, and
        redirecting the distal end of the catheter from the second body lumen to the third body lumen with the aperture opening toward the second body lumen;
    selectively advancing the distal end of the first wire through the catheter and out through the aperture into the second body lumen;
    with the first wire extending through the aperture into the second body lumen, directing, with the catheter, the distal end of the second wire into the third body lumen via
        directing the distal end of the second wire through the catheter and out the distal end of the catheter;
    directing, with the catheter, the distal end of the second wire into the third body lumen and the distal end of the catheter into the second body lumen via
        at least partially withdrawing the first wire from the catheter;
        directing the distal end of the catheter into the second body lumen,
        with the distal end of the catheter maintained in the second body lumen and the aperture opening toward the third body lumen, advancing the first wire through the distal end of the catheter and into the second body lumen, and advancing the second wire through at least a portion of the lumen of the catheter toward the distal end of the catheter, and
        directing the distal end of the second wire out of the lumen of the catheter through the aperture into the third body lumen; and
    directing, with the catheter, the distal end of the second wire and the catheter into the third body lumen and the distal end of the first wire into the second body lumen via
        at least partially withdrawing the first and second wires from the catheter,
        advancing the distal end of the catheter into the third body lumen with the aperture opening toward the second body lumen,
        directing the distal end of the first wire through the aperture and into the second body lumen, and
        directing the distal end of the second wire through the distal end of the catheter into the third body lumen.

2. The method of claim 1, including retracting the first wire from the patient's body while maintaining the catheter in the patient's body.

3. The method of claim 1, including contacting a wall of the second body lumen with the distal end of the first wire to at least partially control a position of the catheter within the patient's body.

4. The method of claim 1, wherein at least a chosen one of the second and third body lumens is an extension of the first body lumen.

5. The method of claim 1, wherein advancing the distal end of the catheter, guided by the associated first wire, through the first body lumen toward an intersection of the first body lumen with second and third body lumens includes:
    placing a dilator inside a lumen of the catheter;
    associating the first wire with the dilator;
    advancing a distal end of the dilator, guided by the associated first wire, through the first body lumen toward an intersection of the first body lumen with second and third body lumens; and
    removing the dilator from the lumen of the catheter.

* * * * *